United States Patent [19]

Baran et al.

[11] Patent Number: 4,707,499

[45] Date of Patent: Nov. 17, 1987

[54] 3-ALKYL-5-(SUBSTITUTED AMINO)METHYL)DIHYDRO-3-PHENYL-2(3H)-FURANONES AND IMINO ANALOGS THEREOF USED FOR TREATMENT OF ARRHYTHMIA

[75] Inventors: John S. Baran, Winnetka; Harman S. Lowrie, Northbrook, both of Ill.

[73] Assignee: G. D. Searle & Co., Chicago, Ill.

[21] Appl. No.: 935,880

[22] Filed: Dec. 1, 1986

Related U.S. Application Data

[62] Division of Ser. No. 803,751, Dec. 2, 1985, abandoned.

[51] Int. Cl.$^4$ ............................................. A61K 31/34
[52] U.S. Cl. ................................... 514/471; 514/472; 514/821
[58] Field of Search ................ 514/471, 472, 473, 821; 549/321, 480

[56] References Cited

U.S. PATENT DOCUMENTS 4,585,789  4/1986  Okamoto et al. ................... 514/473

FOREIGN PATENT DOCUMENTS 576922  6/1959  Canada ................................. 549/321

OTHER PUBLICATIONS

Goodman & Gilman (eds)—The Pharmacological Basis of Theropeutics, 6th ed.–New York–MacMillian Publ. Co., 1980, pp. 730–731, 750–751, 767–786.

*Primary Examiner*—Douglas W. Robinson
*Attorney, Agent, or Firm*—Paul D. Matukaitis; J. Timothy Keane; R. E. L. Henderson

[57]  ABSTRACT

This invention relates to 3-alkyl-5-[(substituted amino)methyl]dihydro-3-phenyl-2(3H)-furanones and imino analogs thereof, and to the pharmaceutical compositions containing such compounds, that are useful as inhibitors of cardiac arrhythmias and are therefore useful in the treatment of irregular heartbeat. This invention also relates to the use of such compounds and pharmaceutical compositions in the treatment of irregular heartbeat.

12 Claims, No Drawings

3-ALKYL-5-(SUBSTITUTED AMINO)METHYL)DIHYDRO-3-PHENYL-2(3H)-FURANONES AND IMINO ANALOGS THEREOF USED FOR TREATMENT OF ARRHYTHMIA

This is a division of application Ser. No. 06/803,751, filed Dec. 2, 1985 now abandoned.

BACKGROUND OF THE INVENTION

This invention relates to novel 3-alkyl-5-[(substituted amino)methyl]dihydro-3-phenyl-2(3H)-furanones and imino analogs thereof, and to the pharmaceutical compositions containing such compounds, that are useful as inhibitors of cardiac arrhythmias and are therefore useful in the treatment of irregular heartbeat. This invention also relates to the use of such compounds and pharmaceutical compositions in the treatment of irregular heartbeat. Some of the compounds of this invention also exhibit antihypertensive activity.

Arrhythmias are disorders relating to electrical impulse generation in the heart. The disorders include premature contractions (extrasystoles) originating in abnormal or ectopic foci in atria or ventricles; atrial flutter; atrial fibrillation; and ventricular tachycardia and fibrillation. For a discussion on these disorders, see, for example, L. S. Goodman and A. Gilman, eds., *The Pharmacological Basis of Therapeutics;* Sixth Edition, New York: Macmillan Publishing Co., 1980; pp. 761–767.

A number of compounds have been developed to alter cardiovascular function related to heart rate and rhythm. The cardiac glycosides, including digitalis, have as their main pharmacodynamic property the ability to increase the force of myocardial contraction. This positive inotropic action is the basis of the salutary effects of these cardiac glycosides in congestive heart failure—increased cardiac output; decreased heart size, venous pressure, and blood volume; and diuresis and relief of edema. Goodman and Gilman at pp. 730–731, 750–751. Quinidine is useful in the therapy of atrial fibrillation but exhibits several toxic reactions, such as cinchonism. Goodman and Gilman at pp. 768–774. Procainamide acts in essentially the same manner as quinidine, and also exhibits toxic side effects. Goodman and Gilman at pp. 774–777. Lidocaine, a widely used local anesthetic, may be used in the treatment of ventricular arrhythmias, but must be administered by injection. Goodman and Gilman at pp. 779–781. Propranolol is useful in the treatment of supraventricular tachycardias and ventricular arrhythmias, but must be used with great care because it may induce significant hypotension, left ventricular failure, or even cardiovascular collapse. Goodman and Gilman at pp. 783–786. Disopyramide has effects somewhat like procainamide and quinidine, all being so-called Type 1 antiarrhythmics. At therapeutic levels disopyramide shortens the sinus node recovery time, lengthens the effective refractory period of the atrium, and has a minimal effect on the refractory period of the A-V node. Goodman and Gilman at pp. 777–779. However, because of the anticholinergic effects of some of the Type 1 antiarrhythmics, such as disopyramide, they should not be used in patients with glaucoma, myasthenia gravis, or problems of urinary retention.

SUMMARY OF THE INVENTION

The invention relates to compounds of Formula I:

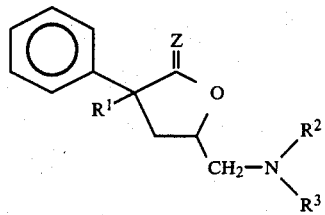

or pharmaceutically acceptable acid addition salts thereof, wherein

Z is =O or =NH;
$R^1$ is alkyl of 1 to 6 carbon atoms, inclusive;
$R^2$ is:
  (a) hydrogen; or
  (b) alkyl of 1 to 6 carbon atoms, inclusive;
$R^3$ is:
  (a) alkyl of 1 to 6 carbon atoms, inclusive; or
  (b) $-(CH_2)_m-NR^4R^5$;
    wherein $R^4$ and $R^5$ are independently alkyl of 1 to 6 carbon atoms, inclusive; and m is an integer from 2 to 6, inclusive.

Examples of alkyl of 1 to 6 carbon atoms, inclusive, are methyl, ethyl, propyl, butyl, pentyl, hexyl, and the isomeric forms thereof, generally referred to as lower alkyl.

A pharmaceutically acceptable acid addition salt is a salt prepared by contacting a compound of Formula I with an acid whose anion is generally considered suitable for human consumption. Examples of pharmacologically acceptable acid addition salts include the hydrochloride, hydrobromide, hydroiodide, sulfate, phosphate, acetate, propionate, lactate, maleate, malate, succinate, and tartrate salts.

DESCRIPTION OF THE INVENTION

The 3-alkyl-5-[(substituted amino)methyl]dihydro-3-phenyl-2(3H)-furanones and imino analogs thereof of this invention may be prepared by the methods illustrated in the following Schemes. Unless otherwise specified, the various substituents are defined as for Formula I, above. Scheme A illustrates a preferred general method for preparing 3-alkyl-5-[(substituted amino)methyl]dihydro-3-phenyl-2(3H)-furanones of this invention.

SCHEME A

2-Phenylalkanoic acids of Formula II are esterified by methods known to those skilled in the art to yield corresponding lower alkyl esters of Formula III.

SCHEME A

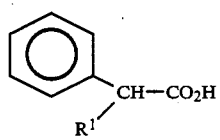

-continued
SCHEME A

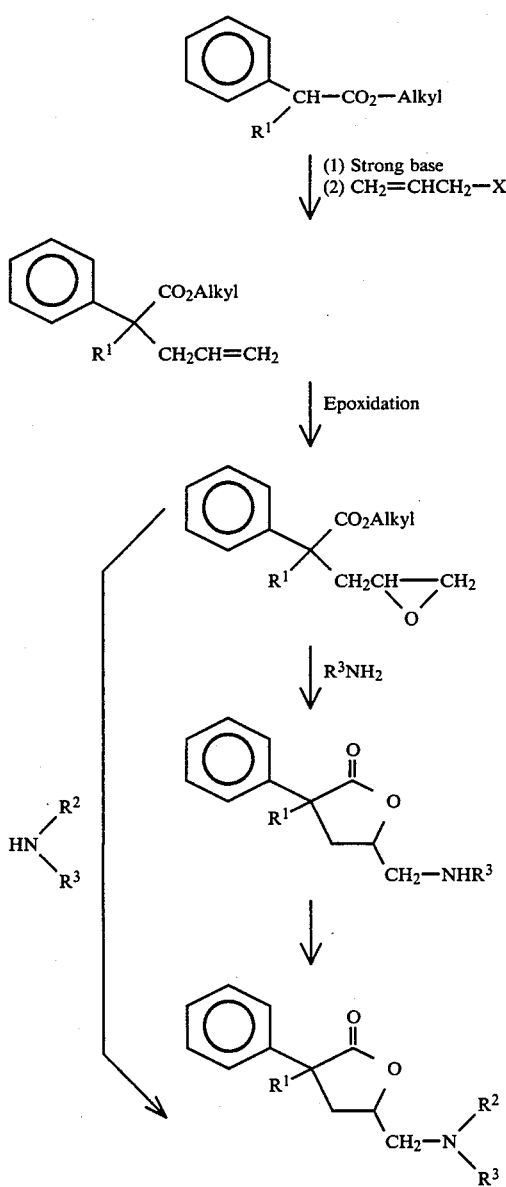

A preferred method includes stirring an acid Formula II in a lower alkanol, preferably methanol or ethanol, containing a catalytic amount of a thionyl halide, preferably thionyl chloride. The resultant ester of Formula III may be isolated by methods known in the art, such as solvent-solvent extraction, and, if necessary, further purified by methods known in the art, such as distillation of liquids or recrystallization of solids.

Compounds of Formula V are prepared by treating esters of Formula III first with strong base in a suitable organic solvent and then with an allyl halide of Formula IV (wherein X is a halogen), preferably allyl bromide. Suitable organic solvents are organic liquids in which reactants may be dissolved or suspended but which are otherwise chemically inert. Suitable organic solvents include alkanes and cycloalkanes, ethers and cyclic ethers, aromatic hydrocarbons, and other such solvents known in the art. A preferred organic solvent is tetrahydrofuran. Strong bases include alkali metal alkoxides, such as sodium methoxide, sodium ethoxide, and potassium t-butoxide; alkali metal alkyls, such as n-butyllithium and t-butyllithium; alkali metal amides, such as sodamide and lithium diisopropylamide; and other such bases known in the art. A preferred strong base is lithium diisopropylamide.

Compounds of Formula V are epoxidized by methods known to those skilled in the art to yield corresponding epoxides of Formula VI. Epoxidation may be effected in organic solvents using hydrogen peroxide, peroxycarboxylic acids, and other such oxidizing agents known in the art. Preferred epoxidation conditions include using m-chloroperbenzoic acid in methylene chloride.

The 3-alkyl-5-[(substituted amino)methyl]dihydro-3-phenyl-2(3H)-furanones of this invention are prepared from epoxides of Formula VI by reaction with suitable amines. In one variation, the epoxides are allowed to react with primary amines of the Formula $R^3NH_2$, wherein $R^3$ is definded as above, to form 3-alkyl-5-[(monosubstituted amino)methyl]dihydro-3-phenyl-2(3H)-furanones of Formula VII. Although the reactions need not be performed in the presence of a solvent, preferred reaction conditions use a lower alkanol, preferably methanol, heated at about 80° to 100° in a pressure vessel. Compounds of Formula VII may then be alkylated to yield 3-alkyl-5-[(disubstituted amino)methyl]dihydro-3-phenyl-2(3H)-furnanones of Formula VIII. Alkylation methods may employ alkyl halides, mesylates, tosylates, and the like, in unreactive organic solvents. Where $R^2$ of Formula VIII is to be methyl, the preferred alkylation method is reductive methylation, in which a compound of Formula VII reacts with a mixture of formic acid and formaldehyde in an organic solvent such as ethanol.

In a second variation of the preparation of 3-alkyl-5-[disubstituted amino)methyl]dihydro-3-phenyl-2(3H)-furanones of Formula VIII, epoxides of Formula VI are allowed to react directly with secondary amines of the Formula $R^2R^3NH$, wherein $R^2$ and $R^3$ are defined as above (using the general method described above to prepare compounds of Formula VIII using primary amines).

Scheme B illustrates an alternative method for preparing 3-alkyl-5-[(substituted amino)methyl]dihydro-3-phenyl-2(3H)-furanones of this invention.

SCHEME B

The 3-alkyl-5-[(substituted amino)methyl]dihydro-3-phenyl-2(3H)-furanones of Formula X are prepared by treating esters of Formula III first with strong base in a suitable organic solvent and then with an epoxide of Formula IX. Suitable organic solvents are organic liquids in which chemical reagents may be dissolved or suspended but which are otherwise chemically inert. Suitable organic solvents include alkanes and cycloalkanes, ethers and cyclic ethers, aromatic hydrocarbons, and other such solvents known in the art. A preferred organic solvent is tetrahydrofuran. Strong bases include alkali metal alkoxides, such as sodium methoxide, sodium ethoxide, and potassium t-butoxide; alkali metal alkyls, such as n-butyllithium and t-butyllithium; alkali metal amides, such as sodamide and lithium diisopropylamide; and other such bases known in the art.

SCHEME B

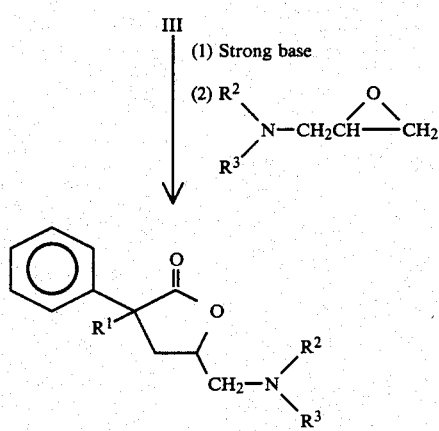

A preferred strong base is lithium diisopropylamide. The epoxides of Formula IX are prepared by the reaction of amines of the Formula $R^2R^3NH$, wherein $R^2$ and $R^3$ are defined as above, with epichlorohydrin or epibromohydrin by methods known in the art. Except for the substitution of epoxides of Formula IX for allyl halides, preferred conditions are the same as described above in Scheme A for the preparation of allyl compounds of Formula V.

Scheme C illustrates a method for preparing N-substituted 4-alkyltetrahydro-5-imino-4-phenyl-2-furanmethanamines of Formula XIII, which are the imino analogs of the 3-alkyl-5-[(substituted amino) methyl]dihydro-3-phenyl-2(3H)-furanones of this invention.

SCHEME C

Epoxides of Formula XII are prepared by the allylation and epoxidation reactions described above and illustrated in Scheme A, except that 2-phenylalkanenitriles of Formula XI are used instead of the esters of Formula III. Reaction of the epoxides of Formula XII with amines of the Formula $R^2R^3NH$ as described above and illustrated in Scheme A, affords N-substituted 4-alkyltetrahydro-5-imino-4-phenyl-2-furanmethanamines of Formula XIII.

SCHEME C

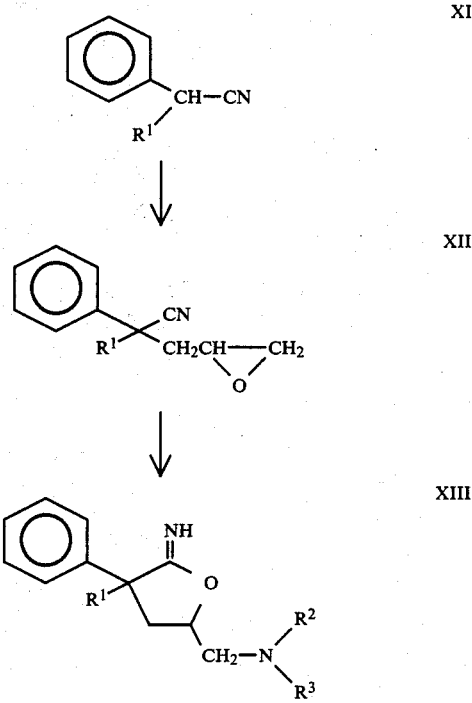

The preferred embodiments of this invention include compounds of the following general structure, Formula XIV

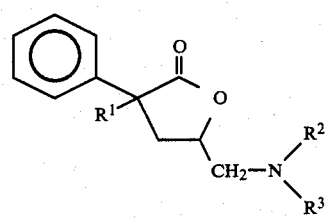

wherein $R^1$ is alkyl of 1 to 6 carbon atoms, inclusive; wherein $R^2$ is hydrogen or alkyl of 1 to 6 carbon atoms, inclusive; and wherein $R^3$ is alkyl of 1 to 6 carbon atoms, inclusive.

The most preferred embodiments of this invention include compounds of the following general structure, Formula XV

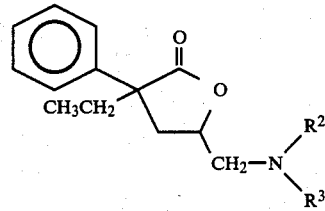

wherein $R^2$ is hydrogen or alkyl or 1 to 6 carbon atoms, inclusive; and wherein $R^3$ is alkyl of 1 to 6 carbon atoms, inclusive.

The compounds of this invention exhibited antiarrhythmic activity in dogs in which ventricular arrhythmia was induced by coronary artery ligation. Arrhythmias induced in this manner are considered similar in nature to those resulting from myocardial infarction in humans. The antiarrhythmic activity of the compounds of this invention illustrated in the examples was tested by the following methods. Quinidine, procainamide, and disopyramide are active under these conditions and are active in man.

Inhibition of Ventricular Arrhythmia Induced by Coronary Ligation

Ventricular arrhythmia was induced by a two-stage ligation of the anterior descending branch of the left coronary artery in each of two or more dogs. Compounds were administered intravenously using an initial 5 mg/kg body weight dose, with additional doses injected at intervals to a maximum of 20 mg/kg. A compound was rated active if it produced at least a 25% reduction in ectopic beats for a period of at least ten minutes in half or more of the dogs. The minimum effective dose that was calculated for each compound is listed in Table A.

TABLE A

| Inhibition of Ventricular Arrhythmia | |
|---|---|
| Compound | Minimum Effective Dose (mg/kg) |
| Example 8 | 5.0 |
| Example 9 | 10.0 |
| Example 11 | 20.0 |

By virtue of their antiarrhythmic activity, the compounds of Formula I are useful in treating arrhythmia in mammals. A physican or veterinarian of ordinary skill can readily determine whether a subject exhibits arrhythmia. Regardless of the route of administration selected, the compounds of the present invention are formulated into pharmaceutically acceptable dosage forms by conventional methods known to those skilled in the art. The compounds may be formulated using pharmacologically acceptable acid addition salts. Moreover, the compounds or their salts may be used in a suitable hydrated form.

The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art.

Accordingly, the invention provides a class of novel pharmaceutical compositions comprising one or more compounds of the present invention in association with one or more non-toxic, pharmaceutically acceptable carriers, diluents, or adjuvants (collectively referred to herein as "carrier" materials) and if desired other active ingredients. The compounds and composition may for example be administered orally, intravascularly, intraperitoneally, subcutaneously, intramuscularly, or topically.

For the therapeutic purposes, the compounds of this invention are ordinarily combined with one or more carriers appropriate to the indicated route of administration. For oral administration, the pharmaceutical composition may be in the form of, for example, a tablet, capsule, suspension, or liquid. The pharmaceutical composition is preferably made in the form of a dosage unit contained in a particular amount of the active ingredient. Examples of such dosage units are tablets or capsules. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, polyvinyl alcohol, or combinations thereof, and thus tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, aqueous sodium chloride, various buffers, or combinations thereof. These oral delivery forms may with advantage contain an amount of active ingredient from about 1 to 250 mg, preferably from about 25 to 150 mg. A suitable daily dose for a mammal may vary widely depending on the condition of the patient and other factors. However, a dose of from about 0.1 to 300 mg/kg body weight, particularly from about 1 to 100 mg/kg body weight, may be appropriate.

The active ingredient may also be administered by injection as a composition wherein, for example, saline, dextrose, or water may be used as a suitable carrier. A suitable daily dose is from about 0.1 to 100 mg per kg body weight injected per day in multiple doses dependig on the disease being treated. A preferred daily dose would be from about 1 to 30 mg/kg body weight.

The dosage regimen for treating cardiac arrhythmia with the compounds or compositions of this invention is selected in accordance with a variety of factors, including the type, age, weight, sex, and medical condition of the patient; the severity of the arrhythmia; the route of administration; and the particular compound employed. Thus, the dosage regimen may vary widely.

The following examples further illustrate details for the preparation of the compounds of this invention. The invention, which is set forth in the foregoing disclosure, is not to be construed or limited either in spirit or in scope by these examples. Those skilled in the art will readily understand that known variations of the conditions and processes of the following preparative procedures can be used to prepare these compounds. All temperatures are degrees Celsius unless otherwise noted. Structure assignments for compounds prepared in the following examples were confirmed by nmr and infrared spectroscopy.

EXAMPLE 1 methyl 2-phenylbutyrate

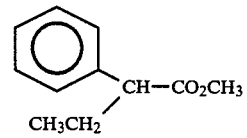

To 102 g. of 2-phenylbutyric acid dissolved in 1 liter of methanol was added 2 ml of thionyl chloride. The solution was allowed to stand at room temperature overnight. The solvent was removed in vacuo to yield an oil which was dissolved in diethyl ether, washed successively with dilute sodium bicarbonate solution and saturated sodium chloride solution, dried over anhydrous potassium carbonate, and concentrated in vacuo. Distillation yielded 101 g of the title compound as a water-white oil, b.p. 62°–65°/0.5 mm, having the following elemental analysis:

For $C_{11}H_{14}O_2$: Calculated: C, 74.12; H, 7.92; Found: C, 73.98; H, 7.97.

EXAMPLE 2:

methyl α-ethyl-α-2-propenylbenzeneacetate

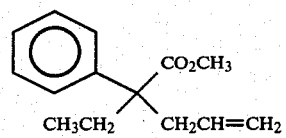

To 15.4 ml of diisopropylamine in 400 ml of dry tetrahydrofuran at −20° to −30° under nitrogen atmosphere was added dropwise with stirring 64.3 ml of a 1.71 M solution of butyllithium in hexane. After stirring 15 min., the mixture was cooled to −70° and a solution of 17.8 g of methyl 2-phenylbutyrate in 100 ml of tetrahydrofuran was added dropwise. After stirring 30 min., a solution of 19.9 ml of allyl bromide in 50 ml tetrahydrofuran was added dropwise; the mixture was stirred and allowed to warm to room temperature overnight. After decomposing with methanol, the reaction mixture was concentrated in vacuo and the residue dissolved in diethyl ether. The ether solution was washed successively with dilute hydrochloric acid, water, dilute sodium bicarbonate, and saturated sodium chloride solution, then dried over anhydrous potassium carbonate and concentrated in vacuo. Distillation of the residue yielded 20.2 g of the title compound as a water-white oil, b.p. 84°–86°/0.45 mm, having the following elemental analysis:

For $C_{14}H_{18}O_2$: Calculated: C, 77.02; H, 8.31; Found: C, 76.80; H, 8.21.

EXAMPLE 3 methyl α-ethyl-α-2-phenyloxiranepropanoate

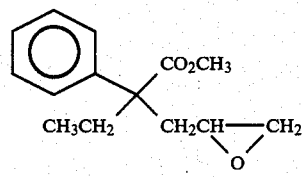

A mixture of 10.2 g of methyl α-ethyl-α-2-propenylbenzeneacetate and 13.0 g of 85% m-chloroperbenzoic acid was stirred in 700 ml of methylene chloride until all solid had dissolved. The resulting solution was allowed to stand at room temperature overnight. The solvent was removed in vacuo, the residue was dissolved in diethyl ether and then washed successively with dilute potassium carbonate and saturated sodium chloride solutions, dried over anhydrous potassium carbonate, and concentrated in vacuo to an oil. The oil was further dried at 40°/1 mm to yield the title compound, which was used in subsequent reactions without further purification.

EXAMPLE 4

3-ethyldihydro-5-[[(1-methylethyl)amino]methyl]-3-phenyl-2(3H)-furanone

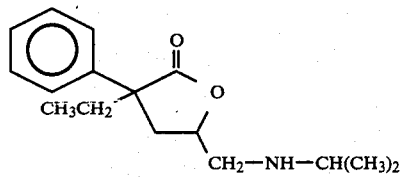

A solution of 1.0 g of methyl α-ethyl-α-2-phenyloxiranepropanoate and 5 g of isopropylamine in 100 ml of methanol was sealed in a pressure bottle and heated in a steam-bath overnight. After cooling, the bottle was opened and the solvent removed in vacuo. The residue was dissolved in diethyl ether, washed with water, and extracted twice with dilute hydrochloric acid. The acid extracts were combined, made basic with dilute sodium hydroxide, and extracted with diethyl ether. The ether solution was washed successively with water and saturated aqueous sodium chloride, dried over anhydrous potassium carbonate, and concentrated in vacuo. The residue, a water-white oil, was dried at 40°/1 mm to yield 0.64 g of the title compound having the following elemental analysis:

For $C_{16}H_{23}NO_2$: Calculated: C, 73.53; H, 8.67; N, 5.36; Found: C, 73.39; H, 8.69; N, 5.09.

The hydrochloride salt was prepared as a white microcrystalline powder by dissolving the free base in tetrahydrofuran, adding hydrogen chloride in dioxane, and precipitating with diethyl ether. EXAMPLES 5–7

Utilizing the appropriate amine starting material instead of isopropylamine, the following compounds were prepared by the procedure of Example 4 from methyl α-ethyl-α-2-phenyloxiranepropanoate. Structure assignments are consistent with the infrared and nmr spectra and with the elemental analyses.

EXAMPLE 5

3-ethyldihydro-5-[(methylamino)methyl]-3-phenyl-2(3H)-furanone, hydrochloride salt

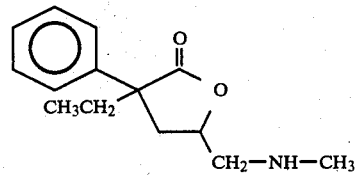

For $C_{14}H_{19}NO_2 \cdot HCl$: Calculated: C, 62.33; H, 7.47; N, 5.19; Found: C, 62.40; H, 7.79; N, 4.94.

EXAMPLE 6

5-[[(1,1-dimethylethyl)amino]methyl]-3-ethyldihydro-3-phenyl-2-(3H)-furanone

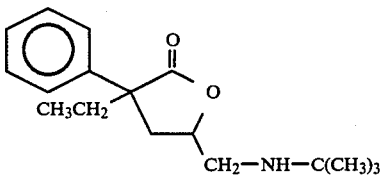

For $C_{17}H_{25}NO_2$: Calculated: C, 74.14; H, 9.15; N, 5.09; Found: C, 74.04; H, 9.07; N, 4.97.

EXAMPLE 7

5-[[[2-(dimethylamino)ethyl]amino]methyl]-3-ethyl-dihydro-3-phenyl-2(3H)-furanone, dihydrochloride salt

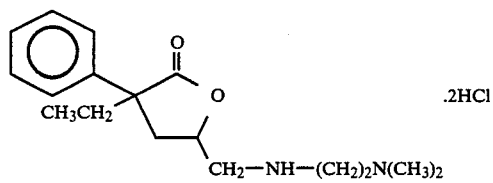

For $C_{17}H_{26}N_2O_2 \cdot 2HCl$: Calculated: C, 56.19; H, 7.77; N, 7.11; Found: C, 55.26; H, 7.44; N, 7.42.

EXAMPLE 8

3-ethyldihydro-5-[[methyl(1-methylethyl)amino]methyl]-3-phenyl-2(3H)-furanone

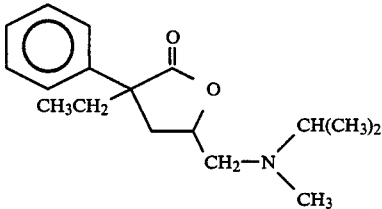

A solution containing 1.3 g of 3-ethyldihydro-5-[[(1-methylethyl)amino]methyl]-3-phenyl-2(3H)-furanone, 1.3 g of 90% formic acid, and 1.1 g of 37% formaldehyde in 15 ml of ethanol was refluxed 2.5 hrs. The solution was cooled and then diluted with water and washed with diethyl ether. The aqueous layer was made basic with dilute sodium hydroxide and extracted with diethyl ether. The ether extract was washed with saturated sodium chloride solution, dried over anhydrous potassium carbonate, and concentrated in vacuo to an oil. The oil was dried at 40°/1 mm to yield 1.0 g of the title compound, having the following elemental analysis:

For $C_{17}H_{25}NO_2$: Calculated: C, 74.14; H, 9.15; N, 5.09; Found: C, 74.16; H, 9.15; N, 4.98.

EXAMPLE 9

5-[[(1,1-dimethylethyl)methylamino]methyl]-3-ethyl-dihydro-3-phenyl-2(3H)-furanone

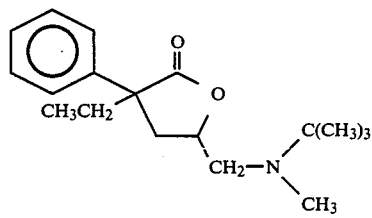

Utilizing 5-[[(1, 1-dimethylethyl)amino]methyl]-3-ethyldihydro-3-phenyl-2(3H)-furanone instead of 3-ethyldihydro-5-[[(1-methylethyl)amino]methyl]-3-phenyl-2(3H)-furanone, the title compound was prepared by the procedure of Example 8.

For $C_{18}H_{27}NO_2$: Calculated: C, 74.70; H, 9.41; N, 4.84; Found: C, 74.68; H, 9.46; N, 4.74.

EXAMPLE 10

3-diisopropylaminopropyl-1,2-epoxide

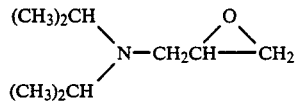

A solution of 202 g of diisopropylamine and 137 g of epibromohydrin in 750 ml of benzene was stirred at reflux for 5 days. The mixture was cooled, diluted with diethyl ether, and filtered. The filtrate was removed in vacuo and the residue distilled to yield the title compound as a water-white oil, b.p. 81°-83°/17 mm, having the expected infrared and nmn spectra. The compound was used in subsequent reactions without further purification.

EXAMPLE 11

5-[[bis(1-methylethyl)amino]methyl]-3-ethyldihydro-3-phenyl-2(3H)-furanone

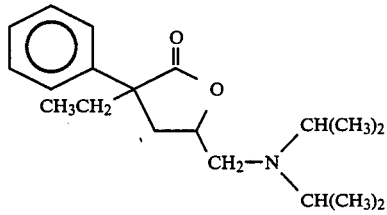

The title compound was prepared according to the method of Example 2, except that 4.3 g of 3-diisopropylaminopropyl-1,2-epoxide (prepared in Example 12) was substituted for allyl bromide, and the quantities of other reactants were adjusted accordingly. After warming to room temperature overnight, the reaction mixture was decomposed with water and concentrated in vacuo, and the resultant residue was dissolved in diethyl ether. The ether solution was washed twice with water, and extracted twice with dilute hydrochloric acid. The acid extracts were combined, made basic with dilute sodium hydroxide, and extracted with diethyl ether. The ether solution was washed with saturated sodium chloride solution, dried over anhydrous potassium carbonate, and concentrated in vacuo to yield the title compound as a yellow oil (7.34 g) having the following elemental analysis:

For $C_{19}H_{29}NO_2$: Calculated: C, 75.20; H, 9.63; N, 4.62; Found: C, 74.62; H, 9.66; N, 4.76.

EXAMPLE 12

α-ethyl-α-phenyloxiranepropanenitrile

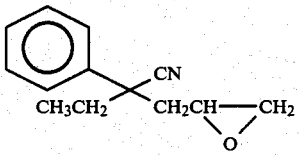

The title compound was prepared by the methods described in Examples 2 and 3 except that 2-phenylbutyronitrile was used instead of methyl 2-phenylbutyrate and complete epoxidation required adding a second quantity of m-chloroperbenzoic acid. The resultant light-yellow oil was used in subsequent reactions without furher purification.

EXAMPLE 13

4-ethyltetrahydro-5-imino-N-(1-methylethyl)-4-phenyl-2-furanmethanamine

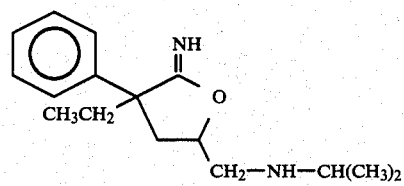

A solution of α-ethyl-α-phenyloxiranepropanenitrile and isopropylamine in ethanol is placed in a pressure bottle and heated overnight in a steam bath. After cooling, the bottle is opened and the solvent removed in vacuo. Solvent-solvent extraction by the method described in Example 4 yields the title compound.

What is claimed is:

1. A method for treating arrhythmia in mammals comprising administering to a mammal in need of such treatment a therapeutically effective amount of a compound of the formula:

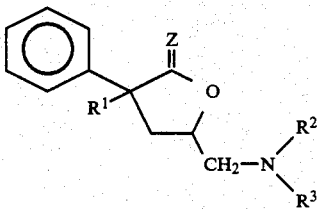

or pharmaceutically acceptable acid addition salts thereof, wherein Z is =O or =NH;
$R^1$ is alkyl of 1 to 6 carbon atoms;
$R^2$ is:
(a) hydrogen; or
(b) alkyl of 1 to 6 carbon atoms;
$R^3$ is:
(a) alkyl of 1 to 6 carbon atoms; or
(b) -$(CH_2)_m$-$NR^4R^5$;
wherein $R^4$ and $R^5$ are independently alkyl of 1 to 6 carbon atoms; and
m is an integer from 2 to 6.

2. A method according to claim 1 wherein said compound is of the formula:

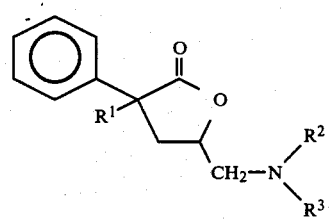

or pharmaceutically acceptable acid addition salts thereof, wherein $R^1$ is alkyl of 1 to 6 carbon atoms;
R2 is:
(a) hydrogen; or
(b) alkyl of 1 to 6 carbon atoms;
$R^3$ is:
(a) alkyl of 1 to 6 carbon atoms; or
(b) -$(CH_2)_m$-$NR^4R^5$;
wherein $R^4$ and $R^5$ are independently alkyl of 1 to 6 carbon atoms; and
m is an integer from 2 to 6.

3. A method according to claim 2 wherein said compound is of the formula:

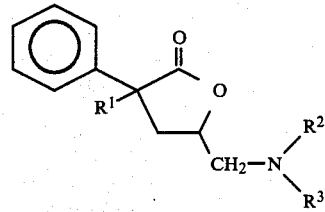

or pharmaceutically acceptable acid addition salts thereof, wherein $R^1$ is alkyl of 1 to 6 carbon atoms;
$R^2$ is:
(a) hydrogen; or
(b) alkyl of 1 to 6 carbon atoms; and
$R^3$ is alkyl of 1 to 6 carbon atoms.

4. A method according to claim 3 wherein said compound is 3-ethyldihydro-5-[(methylamino)methyl]-3-phenyl-2-(3H)-furanone.

5. A method according to claim 3 wherein said compound is 3-ethyldihydro-5-[(dimethylamino)methyl]-3-phenyl-2-(3H)-furanone.

6. A method according to claim 3 wherein said compound is 3-ethyldihydro-5-[[(1-methylethyl)amino]methyl]-3-phenyl-2(3H)-furanone.

7. A method according to claim 3 wherein said compound is 3-ethyldihydro-5-[[methyl(1-methylethyl)amino]methyl]-3-phenyl-2(3H)-furanone.

8. A method according to claim 3 wherein said compound is 5-[[bis(1-methylethyl)amino]methyl]-3-ethyldihydro-3-phenyl-2(3H)-furanone.

9. A method according to claim 3 wherein said compound is 5-[[(1,1-dimethylethyl)amino]methyl]-3-ethyldihydro-3-phenyl-2(3H)-furanone.

10. A method according to claim 3 wherein said compound is 5-[[(1,1-dimethylethyl)methylamino]methyl]-3-ethyldihydro-3-phenyl-2(3H)-furanone.

11. A method according to claim 2 wherein said compound is of the formula:

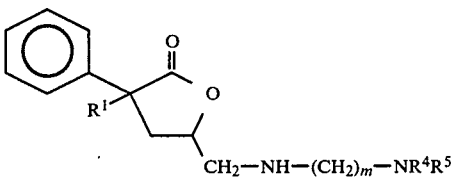

or pharmaceutically acceptable acid addition salts thereof, wherein $R^1$ is alkyl of 1 to 6 carbon atoms;
$R^4$ and $R^5$ are independently alkyl of 1 to 6 carbon atoms; and
m is an integer from 2 to 6.

12. A method according to claim 11 wherein said compound is 5-[[[2-(dimethylamino)ethyl]amino]methyl]-3-ethyldihydro-3-phenyl-2(3H)-furanone.

* * * * *